United States Patent
Pauly

(10) Patent No.: US 10,702,233 B2
(45) Date of Patent: Jul. 7, 2020

(54) DETERMINING A TWO-DIMENSIONAL MAMMOGRAPHY DATASET

(71) Applicant: Siemens Healthcare GmbH, Erlangen (DE)

(72) Inventor: Olivier Pauly, Munich (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 42 days.

(21) Appl. No.: 16/135,061

(22) Filed: Sep. 19, 2018

(65) Prior Publication Data

US 2019/0090834 A1 Mar. 28, 2019

(30) Foreign Application Priority Data

Sep. 28, 2017 (EP) .................................... 17193853

(51) Int. Cl.
*G06K 9/00* (2006.01)
*A61B 6/00* (2006.01)
(Continued)

(52) U.S. Cl.
CPC .............. *A61B 6/502* (2013.01); *A61B 6/025* (2013.01); *G06T 3/0031* (2013.01); *G06T 7/0012* (2013.01); *G06T 15/08* (2013.01); *G06T 7/11* (2017.01); *G06T 7/62* (2017.01); *G06T 11/003* (2013.01); *G06T 2200/04* (2013.01); *G06T 2207/10072* (2013.01); *G06T 2207/10088* (2013.01); *G06T 2207/10112* (2013.01);
(Continued)

(58) Field of Classification Search
None
See application file for complete search history.

(56) References Cited

U.S. PATENT DOCUMENTS 7,760,924 B2 7/2010 Ruth et al.
2017/0011534 A1 1/2017 Costa et al.
(Continued)

FOREIGN PATENT DOCUMENTS

CN 108269292 A 7/2018

OTHER PUBLICATIONS

Radford et al., "Unsupervised representation learning with deep convolutional generative adversarial networks", arXiv: 1511.06434v2 [cs.LG] Jan. 7, 2016 (Year: 2016).*
(Continued)

*Primary Examiner* — Soo Jin Park
(74) *Attorney, Agent, or Firm* — Harness, Dickey & Pierce, P.L.C.

(57) ABSTRACT

A method is for determining a two-dimensional mammography dataset. The method includes the receipt of a three-dimensional mammography dataset of an examination region via an interface. The method furthermore includes the first determination of a two-dimensional mammography dataset of the examination region by application of a trained generator function to the three-dimensional mammography dataset via a processing unit, wherein the trained generator function is based on a trained GA network. Through this method, it is possible efficiently to create two-dimensional mammography datasets, which are visually similar to real two-dimensional mammography datasets and can therefore be appraised with standardized methods.

27 Claims, 7 Drawing Sheets

(51) Int. Cl.
　　　*A61B 6/02*　　　(2006.01)
　　　*G06T 3/00*　　　(2006.01)
　　　*G06T 7/00*　　　(2017.01)
　　　*G06T 15/08*　　(2011.01)
　　　*G06T 11/00*　　(2006.01)
　　　*G06T 7/62*　　　(2017.01)
　　　*G06T 7/11*　　　(2017.01)

(52) U.S. Cl.
　　　CPC ............... *G06T 2207/20076* (2013.01); *G06T 2207/20081* (2013.01); *G06T 2207/20084* (2013.01); *G06T 2207/30068* (2013.01); *G06T 2207/30096* (2013.01); *G06T 2210/41* (2013.01)

(56) References Cited

U.S. PATENT DOCUMENTS

2018/0174049 A1*　6/2018　Pauly ..................... G06N 3/084
2018/0189985 A1　　7/2018　Grimm
2019/0325621 A1*　10/2019　Wang ..................... A61B 6/032

OTHER PUBLICATIONS

Extended European Search Report and English translation thereof dated Mar. 15, 2018.

European Intention to Grant and English translation thereof dated May 24, 2019.

Extended European Search Report dated Mar. 5, 2018 for corresponding European Application No. 17193853.3.

Goodfellow, Ian et al.: "Generative adversarial nets"; in: Advances in Neural Information Processin• Systems, arXiv:1406.2661; 2014.

Diekmann, Felix et al.:"Thick Slices from Tomosynthesis Data Sets: Phantom Study for the Evaluation of Different Algorithms"; in: Journal of Digital Imaging; vol. 22; No. 5; pp. 519-526; Oct. 2009; doi: 10.1007/s10278-007-9075-y.

Van Schie, Guido et al.:"Generating Synthetic Mammograms From Reconstructed Tomosynthesis Volumes"; in: IEEE Transactions on Medical Imaging; vol. 32; No. 12; pp. 2322-2331; Dec. 2013; DOI: 10.1109/tmi.2013.2281738.

Van Schie, Guido et al.: "Mass detection in reconstructed digital breast tomosynthesis volume with a computer-aided detection system trained on 2D mammograms.", in: Medical Physics; vol. 40; No. 4; Apr. 2013; DOI: 10.1118/1.4791643.

Litjens, Geert et al.: "A Survey on Deep Learning in Medical Image Analysis", in: Diagnostic Image Analysis Group, 2017, pp. 1-34; arxiv.org, Cornell University Library, 201OLIN Library Cornell University Ithaca; NY 14853; XP080747655.

Scaduto David A et al: "Determination of System Geometrical Parameters and Consistency between Scans for Contrast-Enhanced Digital Breast Tomosynthesis"; Breast Imaging; Springer Berlin Heidelberg; pp. 24-31; XP047013205; ISBN: 978-3-642-31270-0.

Chinese Office Action and English translation thereof dated Feb. 6, 2020.

* cited by examiner

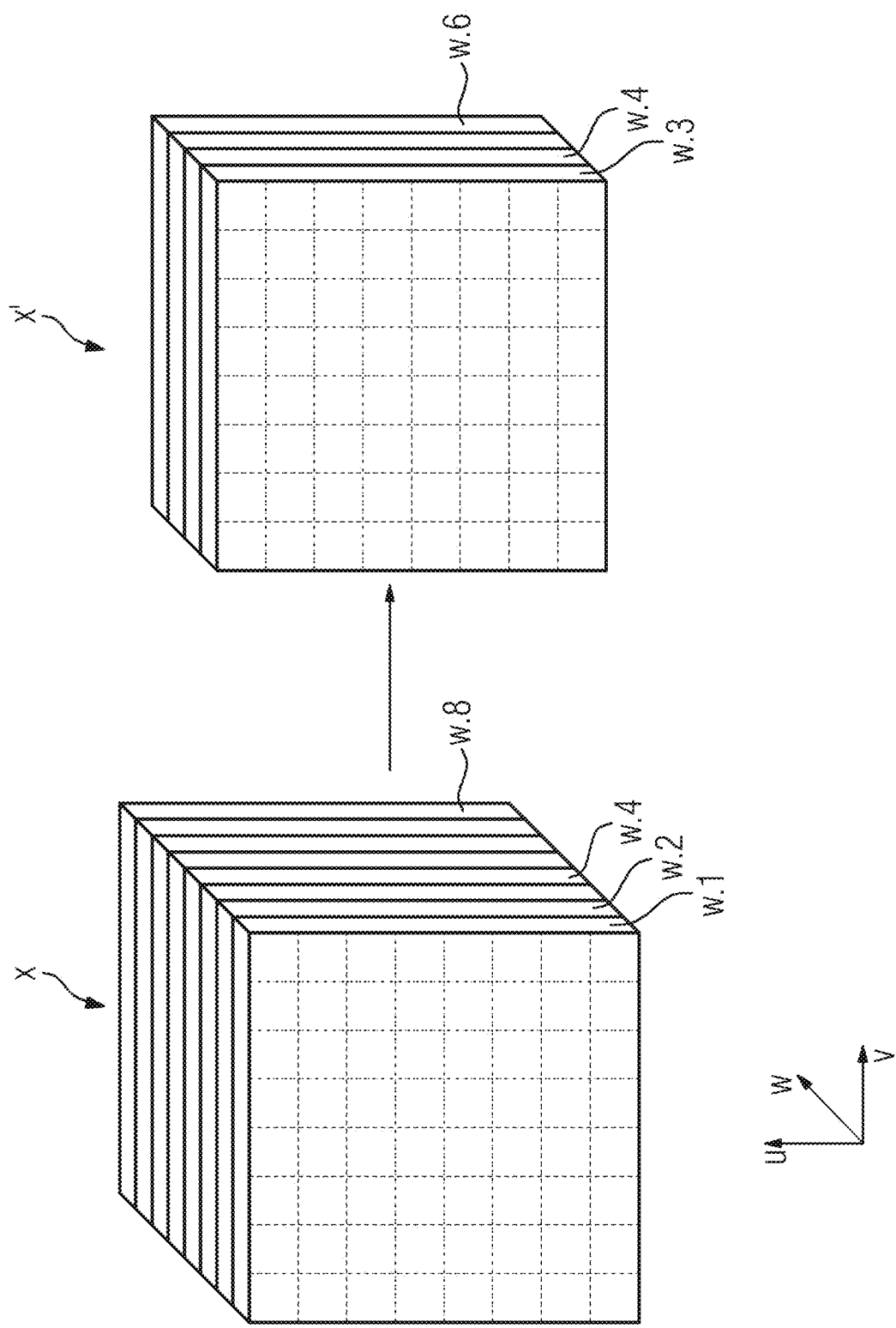

DETERMINING A TWO-DIMENSIONAL MAMMOGRAPHY DATASET

PRIORITY STATEMENT

The present application hereby claims priority under 35 U.S.C. § 119 to European patent application number EP17193853.3 filed Sep. 28, 2017, the entire contents of which are hereby incorporated herein by reference.

FIELD

Embodiments of the invention generally relate to a method for determining a two-dimensional mammography dataset.

BACKGROUND

Digital breast tomosynthesis (DBT) is a promising further development of two-dimensional mammography, which is the standard diagnostic method at present. Since DBT provides three-dimensional information about the breast anatomy, it reduces the number of false positives of two-dimensional mammography, which are caused by the overlaying of fibroglandular tissue. On the other hand however a diagnosis based on digital breast tomosynthesis increases the workload of a doctor making the diagnosis, since a plurality of slice recordings must be inspected.

In order to design the diagnosis, in particular the search for lesions, more efficiently it is advantageous, as well as the digital breast tomography, to continue to provide a two-dimensional mammography. Although the two-dimensional mammography could be provided by a separate recording by way of ionizing radiation, this increases the radiation stress on the tissue being examined. It is therefore advantageous to provide a synthetic two-dimensional mammography dataset based on three-dimensional digital breast tomosynthesis.

The publication by Felix Diekmann et al. "Thick Slices from Tomosynthesis Data Sets: Phantom Study for the Evaluation of Different Algorithms", Journal of Digital Imaging 22(5), P. 519-526 (2009), discloses approaches for creating a two-dimensional mammography dataset, which sum parts of the digital breast tomosynthesis (for example in the form of a Maximal Intensity Projection MIP, or by averaging layers). Although these methods are efficient, they have problems if suspect lesions are hidden behind structures with high intensity values, or when overlapping, inconspicuous structures create false positive results in the projection.

It is known from the publication by G. van Schie et al., "Mass detection in reconstructed digital breast tomosynthesis volumes with a computer-aided detection system trained on 2D mammograms", Medical Physics 40(4), P. 041902 (2013) that a curved two-dimensional surface can be created, which comprises the most conspicuous lesions of digital breast tomosynthesis, and that these can be represented in one plane. However distortions arise from this, so that the resulting two-dimensional image data is dissimilar to a usual two-dimensional mammography and makes a diagnosis difficult.

It is known from the publication US 20170011534 A1 that relevance values can be allocated to voxels of the digital breast tomosynthesis via a self-learning algorithm, wherein the relevance values relate to the relevance of the respective voxel for breast cancer diagnosis. Based on these relevance values, a two-dimensional image dataset is then created by weighted intensity projection. This method of operation is also problematic if suspect lesions are hidden behind structures with high intensity values or when overlapping, inconspicuous structures create false positive results in the projection.

SUMMARY

At least one embodiment of the present invention therefore provides an alternate method for creating a synthetic two-dimensional mammography dataset from a three-dimensional mammography dataset, which also includes the entire three-dimensional mammography dataset in the creation.

Embodiments of the present invention are directed to a method for determining a two-dimensional mammography dataset, a determination system, a computer program product and also a computer-readable storage medium.

Features, advantages of alternate forms of embodiment claimed here are likewise also to be transferred to the other claimed subject matter and vice versa. In other words the physical claims (which are directed to a device for example) can also be developed with the features that are described or explained in conjunction with a method. The corresponding functional features of the method will be embodied in such cases by corresponding physical modules.

At least one embodiment of the present invention relates to a method for determining a two-dimensional mammography dataset. The method comprises the receipt of a three-dimensional mammography dataset of an examination region via an interface. The method further comprises the first determination of a two-dimensional mammography dataset of the examination region by applying a trained generator function to the three-dimensional mammography dataset via a processing unit, wherein the trained generator function is based on a trained GA algorithm.

At least one embodiment of the invention furthermore relates to a determination system, comprising:
interface, embodied for receiving a three-dimensional mammography dataset of an examination region, processing unit, embodied for first determination of a two-dimensional mammography dataset of the examination region through application of a trained generator function to the three-dimensional mammography dataset,
wherein the trained generator function is based on a trained GA network.

At least one embodiment of the invention also relates to a non-transitory computer program product with a computer program and also a non-transitory computer-readable medium. A largely software-based realization has the advantage that determination systems already used previously can also be upgraded in a simple manner by a software update, in order to work in inventive embodiments. Such a computer program product, as well as the computer program, can if necessary comprise additional elements such as e.g. documentation and/or additional components, as well as hardware components, such as e.g. hardware keys (dongles etc.) for use of the software.

At least one embodiment of the invention can also relate to a mammography unit, wherein the mammography unit comprises a previously described embodiments of the determination system.

At least one embodiment of the invention can also relate to a method for providing a generator function, in particular a trained generator function, comprising:
receiving a three-dimensional training mammography dataset of a training examination region, via an interface;

determining a synthetic two-dimensional training mammography dataset of the training examination region by application of a generator function to the three-dimensional training mammography dataset received, via a processor;

determining a first probability value by application of a classifier function to the synthetic two-dimensional training mammography dataset, via the processor;

receiving a real two-dimensional training mammography dataset, via the interface;

determining a second probability value by application of the classifier function to the real two-dimensional training mammography dataset, via the processor; and adjusting parameters of the generator function based on at least one of the first probability value and the second probability value, via the processor.

BRIEF DESCRIPTION OF THE DRAWINGS

The invention will be described and explained in greater detail below with reference to example embodiments shown in the figures and also with reference to dummy code.

FIG. 8 shows the data structure during removal of a two-dimensional layer of the three-dimensional mammography dataset via the processing unit.

DETAILED DESCRIPTION OF THE EXAMPLE EMBODIMENTS

Figure 1:
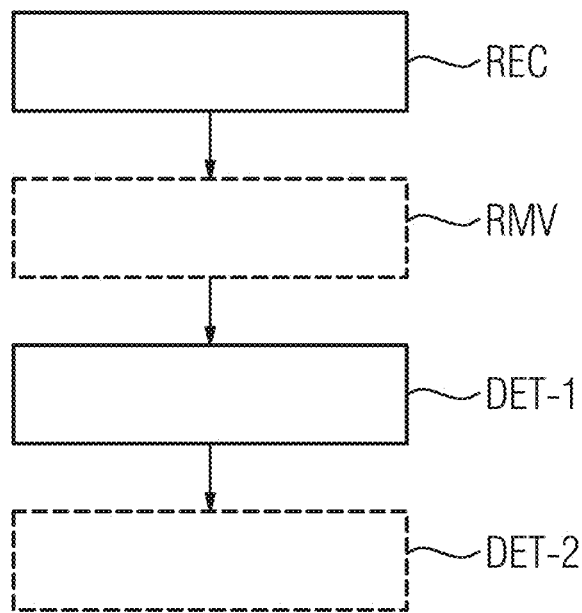
FIG. 1 shows a flow diagram of a method for determining a two-dimensional mammography dataset.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the present invention relates to a method for determining a two-dimensional mammography dataset. The method comprises the receipt of a three-dimensional mammography dataset of an examination region via an interface. The method further comprises the first determination of a two-dimensional mammography dataset of the examination region by applying a trained generator function to the three-dimensional mammography dataset via a processing unit, wherein the trained generator function is based on a trained GA algorithm.

The inventor has recognized that it is possible by this method to create synthetic two-dimensional mammography datasets, which are based on the entire three-dimensional mammography dataset. At the same time two-dimensional mammography datasets, which are visually similar to real two-dimensional mammography datasets and therefore can be appraised with standardized methods, are efficiently created.

According to a further embodiment of the invention, the trained GA algorithm comprises a generative function and a classifying function, wherein the trained generator function is identical to the generative function of the trained GA algorithm. The inventor has recognized that the generator function can be trained especially efficiently and cost-effectively through this structure of the GA algorithm. In particular, the generative function can also be referred to as the generator function, and the classifying function as the classifier function. If the GA algorithm involves a GA network, then the generative function can also be referred to as the generative subnetwork and the classifying function also as the classifying subnetwork.

According to a further embodiment of the invention, the trained generator function is an artificial neural network. In particular the trained generator function is then based on a GA network. The inventor has recognized that the training of an artificial neural network is especially efficient.

In particular, the generative function can also be referred to as the generator function, and the classifying function as the classifier function. If the GA algorithm involves a GA network, then the generative function can also be referred to as the generative subnetwork and the classifying function also as the classifying subnetwork. The generative function, as the generative subnetwork, and the classifying function, as the classifying subnetwork, can both be subnetworks in the case that the GA algorithm is an artificial neural network.

According to a further embodiment of the invention, the trained generator function comprises a concatenation of a first subfunction, a projection function and a second subfunction, wherein the first subfunction maps the three-dimensional mammography dataset to a first feature vector, wherein the projection function maps the first feature vector to the second feature vector, and wherein the second subfunction maps the second feature vector to the two-dimensional mammography dataset. In particular the trained generator function is a concatenation of the first subfunction, of the projection function and of the second subfunction. If the trained generator function is an artificial neural network, then the first subfunction is in particular a first subnetwork, furthermore the projection function is in particular a projection layer, and furthermore the second subfunction is in particular a second subnetwork.

The inventor has recognized that, similarly to an auto encoder, by the mapping to a first and a second feature vector the relevant features of the three-dimensional mammography dataset can be stored as simply and as efficiently as possible, and that by the computation of the two-dimensional mammography dataset based on the first or the second feature vector, these relevant features can be accepted especially easily and efficiently into the two-dimensional mammography dataset.

According to a further possible embodiment of the invention, the first subnetwork and/or the second subnetwork is a convolutional neural network, in particular a deep convolutional neural network. In particular the first subnetwork and/or the second subnetwork can also be a fully convolutional neural network, i.e. in particular not have any fully-linked layers. The inventor has recognized that a convolutional neural network is especially well suited to processing image data efficiently as input values.

According to a further embodiment of the invention, the first subfunction is at least one three-dimensional convolutional operator. When the first subfunction is a first subnetwork, then the three-dimensional convolutional operator is in particular a three-dimensional convolution layer. The inventor has recognized that three-dimensional convolutional operators are especially well suited to recognizing and processing features of three-dimensional image data, in particular in order to construct a feature vector from three-dimensional image data.

According to a further embodiment of the invention, the second subfunction comprises at least one two-dimensional convolutional operator. When the second subfunction is a second subnetwork, then the two-dimensional convolutional operator is in particular a two-dimensional convolution layer. The inventor has recognized that two-dimensional convolutional operators are especially well suited to storing and processing features of two-dimensional image data, in particular in order to construct a two-dimensional image dataset from a feature vector.

According to a further embodiment of the invention, the projection function is a three-dimensional convolutional operator, wherein the two-dimensional mammography dataset is extended in relation to a first direction and in relation to a second direction, wherein the three-dimensional mammography dataset is furthermore extended in relation to a third direction, and wherein the extent of the convolution kernel of the three-dimensional convolutional operator in relation to the third direction is based on the extent of the three-dimensional mammography dataset in relation to the third direction. Here the extent of the convolution kernel and of the three-dimensional mammography dataset are in particular measured in units of pixels.

In particular each of the directions is parallel in each case to an edge of a voxel of the convolution kernel and/or of the three-dimensional mammography dataset. The inventor has recognized that the first feature vector of the three-dimensional mammography dataset can be mapped easily and precisely to the second feature vector of the two-dimensional mammography dataset through this choice of the convolution kernel.

According to a further possible embodiment of the invention, the trained generator function comprises a first subfunction, wherein the first subfunction maps the three-dimensional mammography dataset to a first feature vector, and wherein the first subfunction comprises at least one three-dimensional convolutional operator. In particular, the first subfunction is a first subnetwork and the three-dimensional convolutional operator is a three-dimensional convolution layer. The inventor has recognized that three-dimensional convolutional operators are especially well suited to recognizing and processing features of three-dimensional image data, in particular in order to construct a feature vector from three-dimensional image data.

According to a further possible embodiment of the invention, the trained generator function comprises a second subfunction, wherein the second subfunction maps a second feature vector to the two-dimensional mammography dataset, and wherein the second subfunction comprises at least one two-dimensional convolutional operator. In particular the second subfunction is a second subnetwork and the two-dimensional convolutional operator is a two-dimensional convolution layer. The inventor has recognized that two-dimensional convolution blocks are especially well suited to storing and processing features of two-dimensional image data, in particular in order to construct a two-dimensional image dataset from a feature vector.

According to a further possible embodiment of the invention, the trained generator function comprises a projection function, wherein the projection function maps the first feature vector onto the second feature vector, wherein the projection function is a three-dimensional convolutional operator, wherein the two-dimensional mammography dataset is extended in relation to a first direction and is extended in relation to a second direction, wherein the three-dimensional mammography dataset is furthermore extended in relation to a third direction, and wherein the extent of the convolution kernel of the three-dimensional convolutional operator in relation to the third direction is based on the extent of the three-dimensional mammography dataset in relation to the third direction. In particular each of the directions is parallel in each case to an edge of a voxel of the convolution kernel and/or of the three-dimensional mammography dataset. The inventor has recognized that the first feature vector of the three-dimensional mammography dataset can be mapped easily and precisely to the second feature vector of the two-dimensional mammography dataset through this choice of the convolution kernel.

According to a further embodiment of the invention, the two-dimensional mammography dataset is extended in relation to a first direction and is extended in relation to a second direction, furthermore the method comprises the removal of a two-dimensional layer of the three-dimensional mammography dataset via the processing unit, wherein the two-dimensional layer is extended in relation to the first direction and the second direction. The first direction is in particular orthogonal to the second direction. The inventor has recognized that the trained generator function can be trained especially easily, or that the trained generator function, even with few training data, can create especially precise results, if only three-dimensional mammography datasets with a fixed number of layers are processed. It is therefore advantageous to remove two-dimensional layers from three-dimensional mammography datasets.

According to a further embodiment of the invention, the two-dimensional layer is determined based on the position of the nipple in the three-dimensional mammography dataset. In particular the three-dimensional layer is determined so that the distance of the three-dimensional layer to the position of the nipple is greater than a given threshold value, wherein the distance is measured in pixels or in layers. The inventor has recognized that the central point of the breast can be determined especially easily based on the position of the nipple.

According to a further embodiment of the invention, the two-dimensional layer is determined based on weighting factors of voxels of the three-dimensional mammography dataset. The weighting factors can in particular be specifications as to the probability of a voxel mapping a lesion. In particular the two-dimensional layer is determined so that the distance of the two-dimensional layer to a voxel with an extremal (in particular maximum) weighting factor is greater than a given threshold value, wherein the distance is measured in pixels or in layers. The inventor has recognized that relevant regions of the three-dimensional mammography dataset can be determined especially easily based on weighting factors of voxels.

According to a further embodiment of the invention, the two-dimensional mammography dataset comprises one or more pixels, furthermore the method comprises the second determination of a two-dimensional probability dataset, wherein the two-dimensional probability dataset assigns a probability that the respective pixel is mapping a lesion to each of the one or more pixels of the two-dimensional mammography dataset. The inventor has recognized that an especially easy and fast diagnosis of the two-dimensional mammography dataset is possible, based on the two-dimensional probability dataset.

At least one embodiment of the invention furthermore relates to a determination system, comprising:
  interface, embodied for receiving a three-dimensional mammography dataset of an examination region,
  processing unit, embodied for first determination of a two-dimensional mammography dataset of the examination region through application of a trained generator function to the three-dimensional mammography dataset,
  wherein the trained generator function is based on a trained GA network.

Such a determination system can in particular be embodied to carry out embodiments of the previously described inventive method. The determination system is embodied to carry out this method and its embodiments in that the interface and the processing unit are embodied to carry out the corresponding method steps.

At least one embodiment of the invention also relates to a non-transitory computer program product with a computer program and also a non-transitory computer-readable medium. A largely software-based realization has the advantage that determination systems already used previously can also be upgraded in a simple manner by a software update, in order to work in inventive embodiments. Such a computer program product, as well as the computer program, can if necessary comprise additional elements such as e.g. documentation and/or additional components, as well as hardware components, such as e.g. hardware keys (dongles etc.) for use of the software.

At least one embodiment of the invention can also relate to a mammography unit, wherein the mammography unit comprises a previously described embodiments of the determination system.

At least one embodiment of the invention can also relate to a method for providing a generator function, in particular a trained generator function, comprising:
  first training receipt of a three-dimensional training mammography dataset of a training examination region via an interface,
  first training determination of a synthetic two-dimensional training mammography dataset of the training examination region by application of a generator function to the three-dimensional training mammography dataset via a processing unit,
  second training determination of a first probability value by application of a classifier function to the synthetic two-dimensional training mammography dataset via the processing unit,
  second training receipt of a real two-dimensional training mammography dataset via the interface,
  third training determination of a second probability value by application of the classifier function to the real two-dimensional training mammography dataset via the processing unit,
  adjustment of the parameters of the generator function based on the first probability value and/or the second
  probability value via the processing unit.
  provision of the generator function via the interface.

In particular the parameters of the classifier function can also be adjusted based on the first probability value and/or the second probability value. In particular the adjustment of the parameters of the generator function can furthermore also be based on the synthetic two-dimensional training mammography dataset and/or the three-dimensional training mammography dataset.

A training mammography dataset here can have all features and advantageous developments of a mammography dataset. In particular a synthetic and/or real two-dimensional training mammography dataset can have all features and advantageous developments of a two-dimensional mammography dataset. In particular a three-dimensional training mammography dataset can have all features and advantageous developments of a three-dimensional mammography dataset. A training examination region here can have all features and advantageous developments of an examination region.

A mammography dataset or training mammography dataset is referred to here in particular as synthetic when it is determined from a mammography dataset or from a training mammography dataset with a differing dimensionality. A mammography dataset or training mammography dataset is referred to here in particular as real when it is based on a direct measurement. A three-dimensional training mammography dataset is in particular a real training mammography dataset.

The method for provision of a generator function is a method for training a generator function or a training method of the generator function.

At least one embodiment of the inventive determination system can in particular be embodied to carry out at least one embodiment of the described method for provision of a generator function. The determination system is embodied to carry out the method for provision of a generator function and its embodiments, in that the interface and the processing unit are embodied to carry out the corresponding method steps.

At least one embodiment of the invention can also relate to a non-transitory computer program product with a computer program, which is able to be loaded directly into a memory unit of a determination system, with program sections for carrying out all steps of at least one embodiment of the method for provision of a generator function when the program sections are executed by the determination system.

At least one embodiment of the invention can also relate to a non-transitory computer-readable storage medium, on which program sections able to be read and executed by a determination system are stored, for carrying out all steps of at least one embodiment of the method for provision of a generator function and its embodiments when the program sections are executed by the determination system.

At least one embodiment of the invention can also relate to a non-transitory computer program product or a computer-readable storage medium comprising a trained generator function, wherein the generator function has been trained via at least one embodiment of the method for provision of a generator function.

A mammography dataset is an image dataset of a human breast, in particular of a female breast. A mammography dataset is the result of an x-ray mammography, a magnetic resonance mammography, a tomosynthesis or a mammosonography.

An image dataset comprises at least one image, furthermore an image dataset can also comprise further data, in particular metadata. An image dataset can in particular be identical to the image. A two-dimensional image dataset comprises at least one two-dimensional image, in particular a two-dimensional image dataset does not comprise any further image with a differing dimensionality. A three-dimensional image dataset comprises at least one three-dimensional image, in particular a three-dimensional image dataset does not comprise any further image with a differing dimensionality. A two-dimensional image dataset is in particular identical to a two-dimensional image. A three-dimensional image dataset is in particular identical to a three-dimensional image.

Metadata here is information about the imaging examination, which is the basis for the image dataset, which is not images or image data, for example patient data or data about the protocol used. A dataset or an image dataset is in particular extended in one direction when the extent of the image dataset measured in pixels or voxels is greater than one in this direction. A three-dimensional image dataset, of which the extent measured in voxels in one direction is precisely one, can also be interpreted as a two-dimensional image dataset.

An image dataset comprises a plurality of pixels or voxels. The terms pixel and voxel are used synonymously here, thus in particular do not allow any deductions about a dimensionality. Each of the pixels or the voxels is assigned an intensity value, which preferably corresponds to an x-ray absorption value.

A GA algorithm ("GA" is an acronym for "generative adversarial") comprises a generator function and a classifier function. Here the generator function creates synthetic data and the classifier function distinguishes between synthetic and real data. What is achieved in particular by a training of the generator function and/or of the classifier function is that on the one hand the generator function creates synthetic data, which is incorrectly classified by the classifier function as real, on the other hand the classifier function can distinguish as well as possible between real data and synthetic data. In games theory a GA algorithm can also be interpreted as a zero-sum game. The training of the generator function and/or of the classifier function is based in particular on the minimization of a cost function in each case.

If the generator function and the classifier function are given by a network, in particular by an artificial neural network, then the GA algorithm is also referred to as GA networks (also "GAN", which is an acronym for "generative adversarial networks". These are known in particular from the publication by Ian J. Goodfellow, "Generative Adversarial Networks", arxiv 1406.2661 (2014), the entire contents of which are hereby incorporated herein by reference. The cost function can be minimized in particular by back propagation.

The trained generator function is based in particular on a GA algorithm or on GA networks such that the trained generator function is identical to the generator function of the GA algorithm or of the GA networks.

A function comprises an operator or a subfunction when this function is a concatenation of the operator or of the subfunction with one or more further functions. In particular the first subfunction comprises a three-dimensional convolutional operator when the first subfunction is a concatenation of the three-dimensional convolutional operator with one or more further functions. In particular the second subfunction comprises a two-dimensional convolutional operator when the first subfunction is a concatenation of the two-dimensional convolutional operator with one or more further functions.

A d-dimensional convolutional operator maps a d-dimensional input array to one or more d-dimensional output arrays, by a mathematical convolution with one or more kernels being applied to the d-dimensional input array. The one or more kernels here are also d-dimensional arrays. In particular here the extent of the input array and of the output array is identical in relation to each dimension. A d-dimensional array is in particular a d-dimensional matrix or a d-dimensional image dataset.

A d-dimensional pooling operator maps a d-dimensional input array to a d-dimensional output array, wherein the extent of the output array in relation to at least one dimension is smaller than the extent of the input array in relation to this dimension.

A d-dimensional unpooling operator maps a d-dimensional input array to a d-dimensional output array, wherein the extent of the output array in relation to at least one dimension is smaller than the extent of the input array in relation to this dimension.

Both a d-dimensional convolutional operator and also a d-dimensional pooling operator and a d-dimensional unpooling operator can be realized in an artificial neural network, in particular by two neighboring node layers, wherein the first node layer represents the d-dimensional input array and the second node layer the one or more d-dimensional output arrays. The respective operator is then given by the topology (edges between nodes of the first and the second node layer) and their weights. In this case a d-dimensional convolutional operator is also referred to as a d-dimensional convolution layer, a d-dimensional pooling operator as a d-dimensional pooling layer and a d-dimensional unpooling operator as a d-dimensional unpooling layer. A layer thus comprises in particular two neighboring node layers and all edges between nodes of the two neighboring node layers. Two different layers can have a common node layer, in this case the output value of the first layer serves as the input value of the second layer.

A feature vector is a set of numbers that can be interpreted as a vector. A feature vector can also be a feature channel. In particular a feature vector can also be an image dataset, in particular a two-dimensional or three-dimensional image dataset. In particular the first feature vector can also be a three-dimensional image dataset, and the second feature vector can be a two-dimensional image dataset.

The method of embodiments for determining a two-dimensional mammography dataset and for training a generator function are in particular computer-implemented methods.

FIG. 1 shows a flow diagram of an example embodiment of the method for determining a two-dimensional mammography dataset G_x, G_x'. Optional steps of the method are represented here by dashed lines.

Furthermore Table A shows associated dummy code of the example embodiment.

TABLE A

Dummy code for determining a two-dimensional mammography dataset G_x, G_x'

| | |
|---|---|
| A.1 | func mammo_2d_from_3d(image_3d x, int direction): |
| A.2 | int mid_layer = nipple_layer(x) |
| A.3 | int first_layer = mid_layer − N/2 |
| A.4 | int last_layer = mid_layer + 1 − N/2 |
| A.5 | image_3d x' = select_layers(x, direction, first_layer, last_layer) |
| A.6 | image_2d G_x = G.convert(x') |
| A.7 | image_2d GPM_x = G.probability(x') |
| A.8 | return G_x, GPM_x |

The first step of the example embodiment shown is the receipt REC of a three-dimensional mammography dataset x of an examination region via an interface DS.1. This step corresponds to the line of code A.1. The three-dimensional mammography dataset x here involves a digital breast tomosynthesis. The three-dimensional mammography dataset x comprises voxels arranged in a three-dimensional grid, wherein the extent of the three-dimensional mammography dataset x in a first direction corresponds to L1 voxels, the extent in a second direction corresponds to L2 voxels, wherein the second direction is orthogonal to the first direction, and the extent in a third direction corresponds to L3 voxels, wherein the third direction is orthogonal to the first direction and orthogonal to the third direction. Overall the three-dimensional mammography dataset x thus comprises L1•L2•L3 voxels.

In the example embodiment shown the three-dimensional mammography dataset x also includes information as to which direction of the first direction, the second direction and the third direction is no longer to be present in the two-dimensional mammography dataset G_x, G_x'. In the further description it is assumed that in this case this is the third direction, so that the two-dimensional mammography dataset G_x, G_x' comprises precisely L1•L2 pixels.

The second step of the example embodiment shown is the removal RMV of a two-dimensional layer w.1, w.2, w.7, w.8 of the three-dimensional mammography dataset x via the processing unit DS.2, wherein the two-dimensional layer w.1, w.2, w.7, w.8 is extended in relation to the first direction u and the second direction v. The step of removal RMV is an optional step, it corresponds to the lines of code A.3 to A.5 in the dummy code.

In this example embodiment the two-dimensional layer w.1, w.2, w.7, w.8 is determined based on the position of the nipple in the three-dimensional mammography dataset x (cf. line of code A.2). As an alternative the two-dimensional layer w.1, w.2, w.7, w.8 can be determined based on weighting factors of voxels of the three-dimensional mammography dataset x.

The step of removal RMV of a two-dimensional layer w.1, w.2, w.7, w.8 is explained in more detail in the description for FIG. 8. The result of carrying out the removal one or a number of times is likewise a three-dimensional mammography dataset x'.

The steps described below of the example embodiment are independent of whether the optional step of removal RMV has been carried out. In other words they can be applied both to a three-dimensional mammography dataset x from which no two-dimensional layer w.1, . . . , w.8 has been removed, and also to a three-dimensional mammography dataset x' from which at least one two-dimensional layer w.1, w.2, w.7, w.8 has been removed. However it is advantageous here to adjust a projection function G.PL present in the generator function G to a number of the two-dimensional layers w.1, . . . , w.8 used.

The third step of the example embodiment shown is the first determination DET-1 of a two-dimensional mammography dataset G_x, G_x' of the examination region by application of a trained generator function G to the three-dimensional mammography dataset x, x' via a processing unit DS.2, wherein the trained generator function G is based on a trained GA algorithm. The two-dimensional mammography dataset G_x, G_x' is here in particular a synthetic two-dimensional mammography dataset G_x, G_x'. The step of the first determination DET-1 corresponds to the line of code A.6. Details as well as alternate example embodiments to the step of the first determination DET-1 are explained in the description for FIG. 5.

The generator function G in this example embodiment involves an artificial neural network, but as an alternative the generator function G can also be based on a perceptron, a support vector machine, ("SVM" for short), a random forest or a regression function.

The fourth step of the example embodiment shown is the second determination DET-2 of a two-dimensional probability dataset GPM_x, GPM_x', wherein the two-dimensional probability dataset GPM_x, GPM_x' assigns a probability to each of the one or more pixels of the two-dimensional mammography dataset G_x, G_x' that the respective pixel is mapping a lesion. The second determination DET-2 here is an optional step. The step of the first determination DET-1 corresponds to the line of code A.7. Details and also alternate example embodiments for the step of the second determination DET-2 are explained in the description for FIG. 6.

Figure 2:
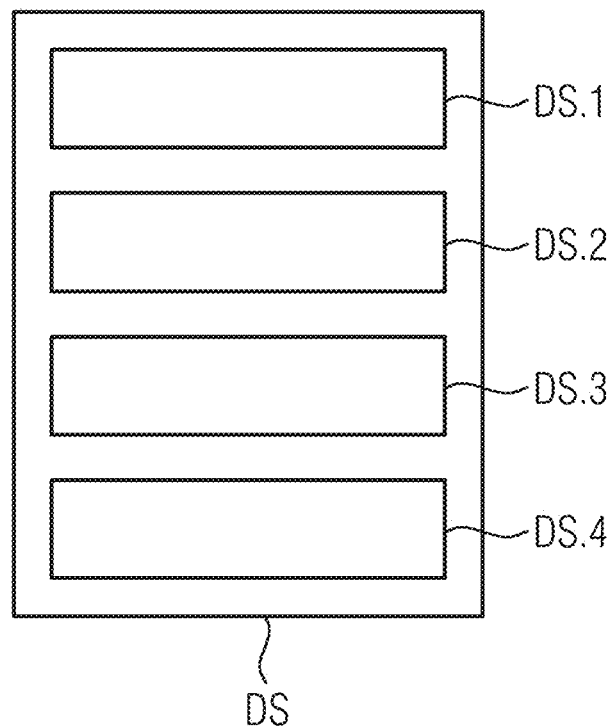
FIG. 2 shows a determination system.

FIG. 2 shows a determination system DS for determining a two-dimensional mammography dataset G_x, G_x'. The determination system DS shown here is designed to carry out embodiments of the inventive method. This determination system comprises an interface DS.1, a processing unit DS.2, a memory unit DS.3 and also an input and output unit DS.4.

The determination system DS can in particular involve a computer, a microcontroller or an integrated circuit. As an alternative the determination system can involve a real network (cluster) or virtual network (Cloud) of computers. In particular the determination system DS can also be part of an imaging mammography unit, as an alternative the determination system DS can also be an imaging mammography unit itself.

An interface DS.1 can involve a hardware or software interface (for example PCI Bus, USB or Firewire). A processing unit DS.2 can have hardware elements or software elements, for example a microprocessor or a so-called FPGA (Field Programmable Gate Array). A memory unit DS.3 can be realized as a Random Access Memory (RAM for short) or as permanent mass storage (hard disk, USB stick, SD card, Solid State Disk). An input and output unit DS.4 comprises at least one input unit and/or at least one output unit.

Figure 3:
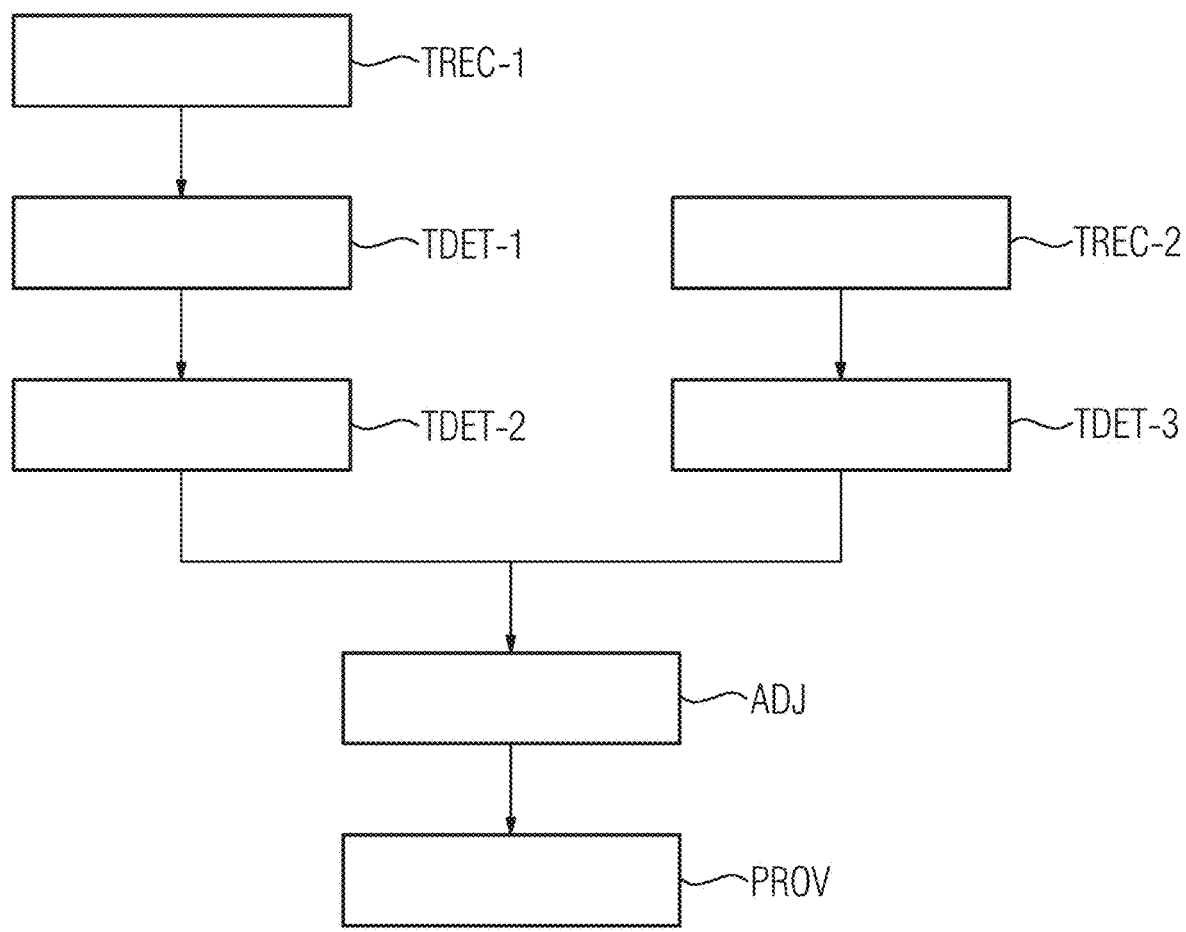
FIG. 3 shows a flow diagram of a method for training a generator function.
Figure 4:
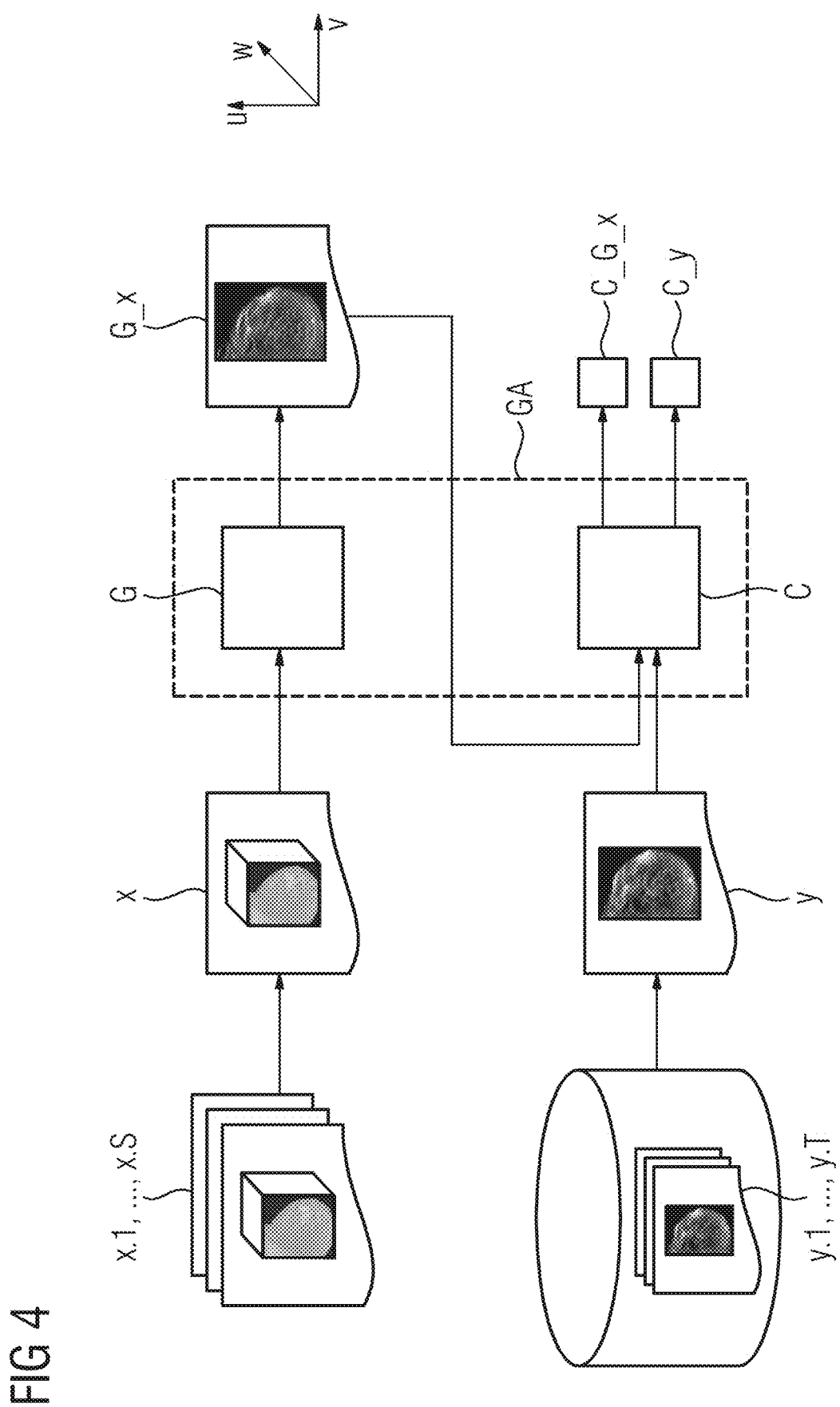
FIG. 4 shows the flow of data of a method for training a generator function.

FIG. 3 shows a flow diagram of a method for provision of a generator function, FIG. 4 shows the flow of data in the method for provision of a generator function G. The generator function G is trained here on the basis of a set of three-dimensional training mammography datasets x.1, . . . , x.S and a set of real two-dimensional training mammography datasets y.1, . . . , y.T.

The generator function is trained step-by-step in this example embodiment, thus only exactly one three-dimensional training mammography dataset x of the three-dimensional training mammography datasets x.1, . . . , x.S and exactly one real two-dimensional training mammography dataset y of the real two-dimensional training mammography datasets y.1, . . . , y.T are used simultaneously in each training step, but this training step can be repeated any number of times, in order to obtain a better-trained function G. As an alternative it is also possible to use a number of the three-dimensional training mammography datasets x.1, . . . , x.S and/or a number of the real two-dimensional T training mammography datasets y.1, . . . , y.T in a training step.

The first step of the method shown is the first training receipt TREC-1 of a three-dimensional training mammography dataset x of a training examination region via an interface DS.1. The three-dimensional training mammography dataset x here is one of the three-dimensional training mammography datasets x.1, . . . , x.S.

The second step of the method shown is the first training determination TDET-1 of a synthetic two-dimensional mammography dataset G_x of the training examination region by application of the generator function G to the three-dimensional training mammography dataset x via a processing unit DS.2. Here the three-dimensional training mammography dataset x is the input value of the generator function G, the synthetic two-dimensional mammography dataset G_x is the output value G(x) created by the generator function G.

A classifier function C will furthermore be needed for training the generator function G. The classifier function C maps a real two-dimensional training mammography dataset y or a synthetic two-dimensional mammography dataset G_x to a real number between 0 and 1, in particular to a probability value. This probability value corresponds to the probability that the input dataset of the classifier function C is an element of the set of two-dimensional training mammography datasets y.1, . . . , y.T. The generator function G and the classifier function C together with suitable cost functions form a GA network.

The third step of the example embodiment shown is the second training determination TDET-2 of a first probability value C_G_x by application of the classifier function C to the synthetic two-dimensional mammography dataset G_x via the processing unit DS.2. Here the classifier function C obtains the synthetic two-dimensional mammography dataset G_x as its input value and creates the first probability value C_G_x as its output value.

The fourth step of the example embodiment shown is the second training determination TDET-2 of a real two-dimensional training mammography dataset y via the interface DS.1. The real two-dimensional training mammography dataset y here is one of the real two-dimensional training mammography datasets y.1, . . . , y.T.

The fourth step of the example embodiment shown is the third training determination TDET-3 of a second probability value C_y by application of the classifier function C to the real two-dimensional training mammography dataset y via the processing unit DS.2. Here the classifier function C obtains a real two-dimensional mammography dataset y of the two-dimensional training mammography datasets y.1, . . . , y.T as its input value, and creates the second probability value C_y as its output value.

The steps of the first training receipt TREC-1, of the first training determination TDET-1 and of the second training determination TDET-2 are carried out here in the order listed, they form a first group. Furthermore the steps of the second training receipt TREC-2 and of the third training determination TDET-3 are carried out in the order listed, they form a second group. These two groups of steps are independent of one another however, i.e. the steps of the second training receipt TREC-2 and of the third training determination TDET-3 can also be carried out in each case before one of the steps of the first training receipt TREC-1, of the first training determination TDET-1 and of the second training determination TDET-2. In particular the steps of the first training receipt TREC-1 and of the second training receipt TREC-2 can be carried out in each case before the steps of the first training determination TDET-1, of the second training determination TDET-2 and of the third training determination TDET-3.

The sixth step of the example embodiment shown is the adjustment ADJ of the parameters of the generator function G based on the first probability value C_G_x and on the second probability value C_y. In particular here parameters of the classifier function C are also adjusted. In this example embodiment two cost functions, which depend on C_G_x and C_y will be minimized for this by adjustment of parameters of the generator function G and of the classifier function C. By a suitable choice of the cost function the generator function G is trained so that the classifier function C cannot decide whether G_x is chosen from the set of real two-dimensional training mammography datasets y.1, . . . , y.T, i.e. C_G_x=0.5. This gives rise to the technical term "generative-adversarial" of the training method, since the generator function G creates synthetic data ("generative"), and the generator function G and the classifier function C are trained against each other ("adversarial").

Possible cost functions of the generator function G and of the classifier function C are each described below. Naturally it is however possible to use other cost functions at any time.

The cost function KC of the classifier function C is given in this example embodiment by $$K_C \propto \mathrm{BCE}(C\_y, 1) + \mathrm{BCE}(C\_G\_x, 0)$$

wherein BCE refers to the binary cross-entropy:

$$\mathrm{BCE}(z, z') = z' \cdot \log(z) + (1-z') \cdot \log(1-z)$$

Thus the cost function $K_c$ of the classifier function C is given in particular by:

$$K_c(C\_y, C\_G\_x) \propto \log(C\_y) + \log(1 - C\_G\_x)$$

It is likewise possible to carry out a training step not only with a three-dimensional training mammography dataset x and on the real two-dimensional training mammography dataset y, but also with a number of three-dimensional training mammography datasets and/or a number of real two-dimensional training mammography datasets. In this case the cost function is given by $$K_c \propto \frac{1}{J} \sum_{j=1}^{J} \log(c\_y_j) + \frac{1}{I} \sum_{i=1}^{I} \log(1 - C\_G\_x_i)$$

wherein I refers to the number of three-dimensional training mammography datasets used (with I≥S), wherein J refers to the number of real two-dimensional training mammography datasets used (with J≥T), wherein $C\_y_j$ refers to the application of the classifier function C to the jth real two-dimensional training mammography dataset, and wherein $C\_G\_x_i$ refers to the application of the classifier function C to the result of the application of the generator function to the ith three-dimensional training mammography dataset.

The cost function $K_G$ for the generator function G is given by $$K_G = \alpha \cdot K_{proj} + \beta \cdot K_{cont} + \gamma \cdot K_{adver},$$

wherein the share $K_{proj}$ quantifies a deviation of the synthetic two-dimensional mammography dataset G_x from a projection of the three-dimensional training mammography dataset x, wherein $K_{cont}$ gives preference to a large difference in contrast between a region with a lesion and the environment, and wherein $K_{adver}$ is selected such that the classifier function classifies the synthetic two-dimensional training mammography datasets y.1, . . . , y.T as real. The parameters α, β and γ are real numbers, which can be freely selected for weighting the individual contributions to the cost function. In the present example embodiment the parameters are chosen as α=β=γ=1. The share $K_{cont}$ is optional here (thus β=0 can be selected).

The deviation of the synthetic two-dimensional mammography dataset G_x from a projection of the three-dimensional training mammography dataset x can be quantified for example by the following share $K_{proj}$:

$$K_{proj}(x) = [Pr(x) - G(x)]^2$$

If a number of training datasets are used in a training step, then the share $K_{proj}$ of the cost function $K_G$ is averaged over the number of training datasets:

$$K_{proj}(x_1, \ldots, x_N) = \frac{1}{N} \cdot \left( \sum_{n=1}^{N} [Pr(x_n) - G(x_n)]^2 \right)$$

Here Pr(x) refers to the application of a projection operator to the three-dimensional training mammography dataset x, in particular of a projection operator in relation to the third direction w, wherein the projection operator maps a three-dimensional dataset to a two-dimensional dataset. In this example embodiment the projection operator is a maximal intensity projection (MIP for short) in relation to the third direction x as projection direction. As an alternative it can also involve a projection to an average value in the projection direction or a multi planar reformat, (MPR for short).

What is achieved by this contribution in the cost function KG is that the three-dimensional training mammography dataset x is mapped to a synthetic two-dimensional mammography dataset G_x, which also actually corresponds to a two-dimensional projection Pr(x) of the three-dimensional training mammography dataset x, and is not just similar to a real two-dimensional training mammography dataset y.1, . . . , y.T.

Through the following contribution $K_{cont}$ to the cost function $K_G$ a high contrast between regions of the image which comprise a lesion and the remaining regions of the image can be achieved:

$$K_{cont}(x, m) = -\text{SNR}(Pr(m), G(x))$$

If a number of training data records are used in a training step, then the share $K_{proj}$ of the cost function $K_G$ is averaged over the number of training data records:

$$K_{cont}(x_1, \ldots, x_N, m_1, \ldots, m_N) = -\frac{1}{N} \cdot \left( \sum_{n=1}^{N} \text{SNR}(Pr(m_n), G(x_n)) \right)$$

Here m or $m_n$ refers to a training segmentation of the three-dimensional training mammography dataset x or $x_n$, in which one or more lesions were segmented in the three-dimensional training mammography dataset x or $x_n$. The training segmentation here comprises voxels, to which the value 1 is assigned when the respective voxel maps a lesion, and to which the value 0 is assigned when the respective voxel does not map a lesion. The projection function here can also again be a maximal intensity projection, the projection function can furthermore also depend on the three-dimensional training mammography dataset x. For example the projection function can calculate a maximal intensity projection such that the relevant voxels with the maximal intensity will be determined based on the three-dimensional training mammography dataset x, but then the pixel values of the training segmentation m will be projected. In particular Pr(m) is thus a two-dimensional segmentation.

The function SNR refers here to a signal-to-noise ratio, in this example embodiment the function is given by $$\text{SNR}(Pr(m), G(x)) = \frac{L_1 L_2 - \Sigma Pr(m)}{\Sigma Pr(m)} \cdot \frac{Pr(m) \cdot G(x)}{[1 - Pr(m)] \cdot G(x)}$$

wherein the product of two-dimensional datasets or images is interpreted in pixels. Here $L_1$ refers to the extent of the datasets in the first direction u, and L2 to the extent of the datasets in the second direction v, and ΣPr(m) refers to the number of pixels in Pr(m) to which a 1 is assigned as their intensity. The function SNR here thus calculates the ratio of the average of the intensity values of G_x in the segmented region to average of the intensity values of G_x outside of the segmented region. As an alternative the function SNR can also be based on the standard deviations of the intensity values of G_x outside of the segmented region.

The minimization of the contribution $K_{cont}$ to cost function $K_G$ thus leads to lesions in the synthetic two-dimensional mammography dataset G_x being characterized by high intensity values, and therefore being able to be diagnosed especially easily.

The contribution $K_{adver}$ to cost function $K_G$ leads to the generated synthetic two-dimensional mammography datasets G_x being as similar as possible to the real two-dimensional training mammography datasets y.1, . . . , y.T, in that the synthetic two-dimensional mammography datasets G_x are generated such that the classifier function cannot distinguish these from the real two-dimensional training mammography datasets y.1, . . . , y.T. The binary cross-entropy can again be selected for this contribution $$K_{adver}(C\_G\_x) = BCE(C\_G\_x, 1) = -\log(C\_G\_x) = -\log(C(G(x)))$$

wherein here too there can again be averaging over a number of training data records:

$$K_{adver}(G\_C\_x_1, \ldots, G\_C\_x_N) = -\frac{1}{N} \cdot \left( \sum_{n=1}^{N} \log(G\_C\_x_n) \right)$$

The optimization is thus undertaken here so that a high first probability value G_C_x close to 1 minimizes the cost function.

When the generator function G based on a three-dimensional training mammography dataset x also creates a probability dataset GPM_x as well as a synthetic two-dimensional mammography dataset G_x, the cost function $K_G$ can also depend additively on the contribution $K_{cont}$, which measures the similarity between the probability dataset GPM_x and the projected segmentation. A possible choice for this term is $$K_{segm}(x, m) = 1 - 2 \cdot \frac{GPM(x) \cdot Pr(m)}{GPM(x) \cdot GPM(x) + Pr(m) \cdot Pr(m)}$$

wherein GPM(x) refers to the probability dataset belonging to the three-dimensional training mammography dataset x, and wherein the product is to be understood as pixels. This term too can be averaged in each case over a number of training images:

$$K_{segm}(x_1, \ldots, x_N, m_1, \ldots, m_N) =$$
$$1 - \frac{2}{N} \sum_{n=1}^{N} \frac{GPM(x_n) \cdot Pr(m_n)}{GPM(x_n) \cdot GPM(x_n) + Pr(m_n) \cdot Pr(m_n)}$$

This contribution is based on the Sorensen-Dice coefficient. As an alternative this contribution can however also be based on the Jaccard index or the Tversky index for example.

In this example embodiment the parameter generator function G and the classifier function C will be adjusted by minimization of the cost functions KG and KC by back propagation. Back propagation for artificial neural networks is known here to the person skilled in the art, therefore a more detailed description will not be provided here.

The last step of the example embodiment shown is the provision PROV of the generator function G via the interface DS.1.

TABLE B

Dummy code for provision of a generator function

| | |
|---|---|
| B.1 | G.init(G__params__initial) |
| B.2 | C.init(C__params__initial) |
| B.3 | a = 0.01 |
| B.4 | func train(network G, network C, image__3d x, image__3d m, image__2d y): |
| B.5 | image__2d G__x = G.convert(x) |
| B.6 | float C__y = C.apply__to(y) |
| B.7 | C.params −= a*back__prop(C, C.loss(1, C__y)) |
| B.8 | float C__G__x = C.apply__to(G__x) |
| B.9 | C.params −= a*back__prop(C, C.loss(0, C__G__x)) |
| B.10 | C__G__x = C.apply__to(G__x) |
| B.11 | G.params −= a*back__prop(G, G.loss(C__G__x, m, x)) |

Table B shows dummy code for the example embodiment for determining a generator function G shown in FIG. 3 and FIG. 4. In the lines of code B.1 and B.2 the generator function G and the classifier function C are initialized as artificial neural networks with standard parameters. The learning speed "a" quantifies the speed of the learning process and is initialized in line B.3.

In line of code B.4 the function "train" is declared, which applies a training step to the generator function G and the classifier function C, which is based on a three-dimensional training mammography dataset x and on the real two-dimensional training mammography dataset y. The function call of this function implements the steps of the first training receipt TREC-1 and of the second training receipt TREC-2.

In line of code B.5 a synthetic two-dimensional mammography dataset G_x is created by application of the generator function G to the three-dimensional training mammography dataset x. This corresponds to the method step of the first training determination TDET-1.

In lines of code B.6 a second probability value C_y is determined by application of the classifier function C to the real two-dimensional training mammography dataset y. This corresponds to the method step of the third training determination TDET-3. In line of code B.7 the parameters of the classifier function C are adjusted, in that the cost function is minimized by back propagation. The cost function here corresponds to the binary-cross entropy. This line of code corresponds to a part of the method step of the adjustment ADJ.

In lines of code B.8 a first probability value C_G_x is determined by application of the classifier function C to the synthetic two-dimensional mammography dataset G_x. This corresponds to the method step of the second training determination TDET-3. In line of code B.9 the parameters of the classifier function C are adjusted, in that the cost function is minimized by back propagation. The cost function corresponds here to the binary-cross entropy. This line of code corresponds to a part of the method step of the adjustment ADJ.

In the lines of code B.10 and B.11 the first probability value C_G_x is determined once more by application of the classifier function C to the synthetic two-dimensional mammography dataset G_x. Since the parameters of the classifier function C have been adjusted in line of code B.9, the numerical value of the first probability value changes. The parameters of the generator function G are adjusted in line of code B.11, in that the cost function of the generator function G is minimized by back propagation. The cost function here corresponds to the already defined function $K_G$. This line of code corresponds to a part of the method step of the adjustment ADJ.

Figure 5:
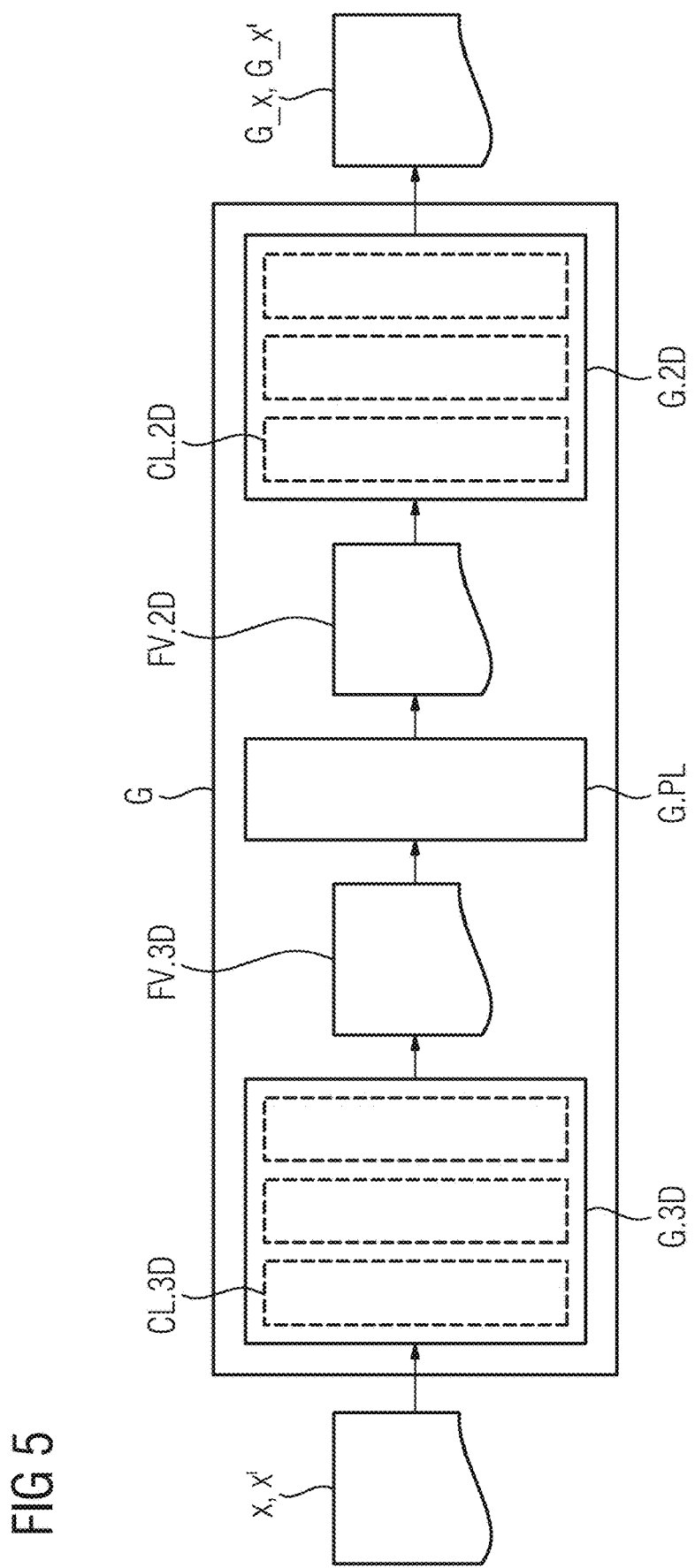
FIG. 5 shows a first example embodiment of a generator function.

FIG. 5 shows a first example embodiment of a generator function G, which is embodied as an artificial neural network. In this example embodiment the generator function comprises a first subnetwork G.3D, a second subnetwork G.2D, and also a projection layer G.PL. The first subnetwork maps a three-dimensional mammography dataset x, x' to a first feature vector FV.3D. The projection layer G.PL maps the first feature vector FV.3D to a second feature vector FV.2D. The second subnetwork G.2D maps the second feature vector FV.2D to a synthetic two-dimensional mammography dataset G_x, G_x'.

The input value of the generator function G here is either a first two-dimensional mammography dataset x, when the optional step of the removal has not been applied beforehand to the first two-dimensional mammography dataset x, or a second mammography dataset x', when the optional step of the removal has been applied beforehand to the first two-dimensional mammography dataset x.

Both the first subnetwork G.3D and also the second subnetwork G.2D are convolutional neural networks in this example embodiment.

The first subnetwork G.3D in this example embodiment comprises a number of three-dimensional convolution layers CL.3D, the second subnetwork G.2D in this example embodiment comprises a number of two-dimensional convolution layers CL.2D. The first subnetwork G.3D in this example embodiment furthermore comprises at least one pooling layer, the second subnetwork G.2D in this example embodiment furthermore comprises at least one unpooling layer.

Advantageously the first subnetwork G.3D and/or the second subnetwork G.2D comprise one or more inception modules. An inception module combines at least two convolutional operators with convolution masks of different sizes into a common output value. The use of inception modules is known for example from the network architecture "GoogLeNet", through this the sizes of the convolution masks in the respective layers do not have to be predetermined, but can be selected automatically in the learning process from a number of options. Furthermore the first subnetwork G.3D, the second subnetwork G.2D can comprise residual connections.

In the example embodiment shown the two-dimensional mammography dataset G_x, G_x' is extended in relation to a first direction u and in relation to a second direction v, wherein the three-dimensional mammography dataset x, x' is furthermore extended in relation to a third direction w. The projection layer G.PL, in the example embodiment shown, is a three-dimensional convolutional operator or a three-dimensional convolution layer CL.3D, wherein the extent of the convolution kernel in relation to the third direction w is based on the extent L3 of the three-dimensional mammography dataset x, x' in relation to the third direction w. In particular the convolutional operator is selected so that the output value in relation to the third direction w only has an extent of one voxel, thus in particular maps a three-dimensional value into a two-dimensional value. In particular the extent of the convolution kernel in relation to the third direction w is identical to the extent of the input value of the convolutional operator in relation to the third direction w, this corresponds to the extent L3 of the third mammography dataset x, x', which has been corrected based on the effects of the pooling and unpooling layers of the first subnetwork G.3D on the extent of the dataset in relation to the third direction w.

Figure 6:
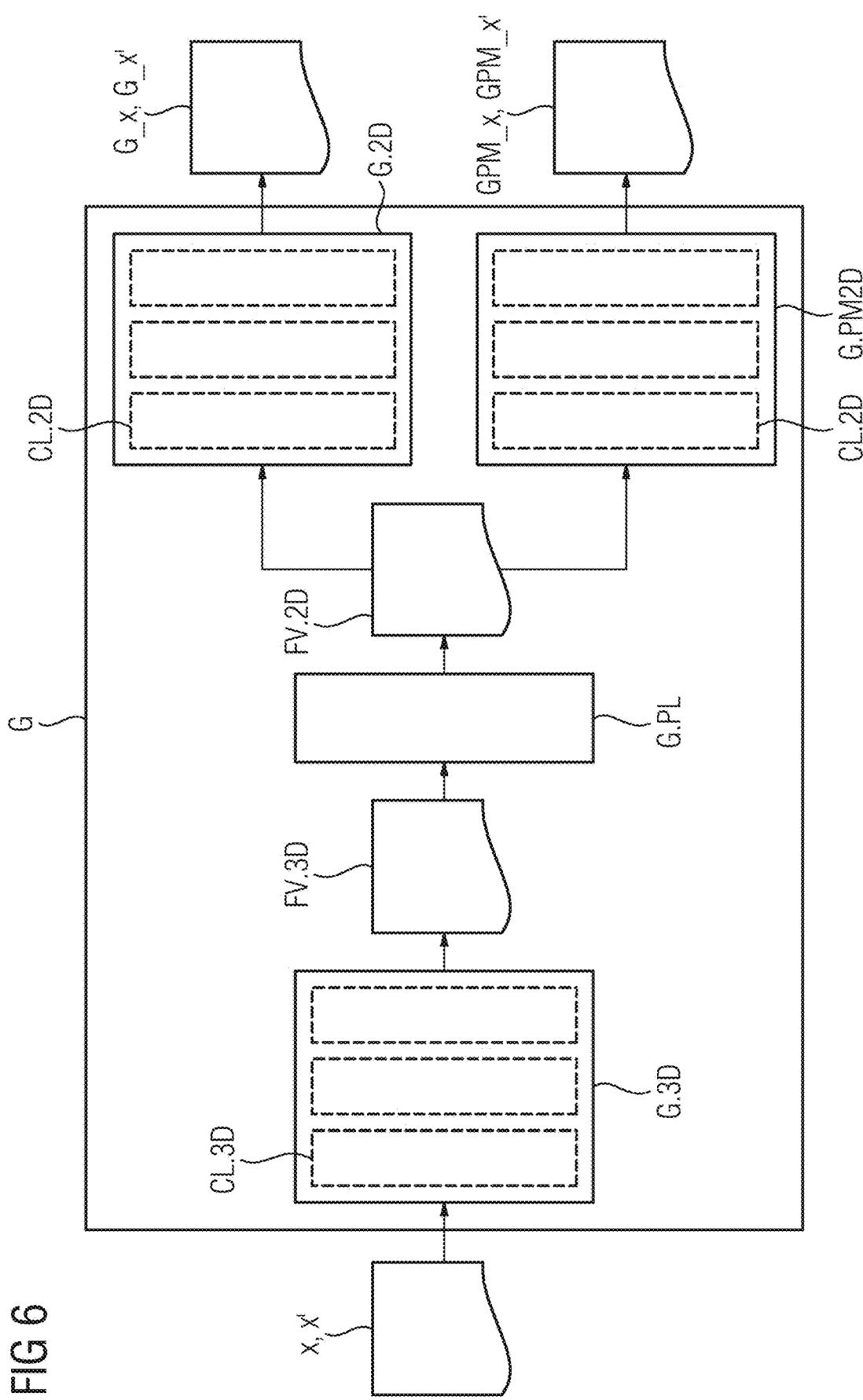
FIG. 6 shows a second example embodiment of a generator function.

FIG. 6 shows a second example embodiment of a generator function G. In this example embodiment the generator function comprises a first subnetwork G.3D, a second subnetwork G.2D, a projection layer G.PL, and also a third subnetwork PM.3D. The first subnetwork maps a three-dimensional mammography dataset x, x' to a first feature vector FV.3D. The projection layer G.PL maps the first feature vector FV.3D to a second feature vector FV.2D. The second subnetwork G.2D maps the second feature vector FV.2D to a synthetic two-dimensional mammography dataset G_x, G_x'. The third subnetwork G.PM2D maps the second feature vector FV.2D to a probability dataset GPM_x, GPM_x', wherein the probability dataset GPM_x, GPM_x' assigns to each pixel of the synthetic two-dimensional mammography dataset G_x, G_x' a probability value of between 0 and 1. In other words the probability dataset GPM_x, GPM_x' can therefore also be interpreted as the image dataset.

The first subnetwork G.3D and the second subnetwork G.2D as well as the projection layer G.PL can have the features and advantageous developments described in the description for FIG. 5.

The third subnetwork G.PM2D in this example embodiment has one or more two-dimensional convolution layers CL.2D. Advantageously the third subnetwork G.PM2D can have pooling layers and unpooling layers. Furthermore the third subnetwork G.PM2D can comprise residual connections.

In this example embodiment the output value of the generator function G is a pair comprising a synthetic two-dimensional mammography dataset G_x, G_x' as well as a two-dimensional probability dataset GPM_x, GPM_x'. The notation G(x), G(x') however also refers in this case just to the synthetic two-dimensional mammography dataset G_x, G_x'.

Figure 7:
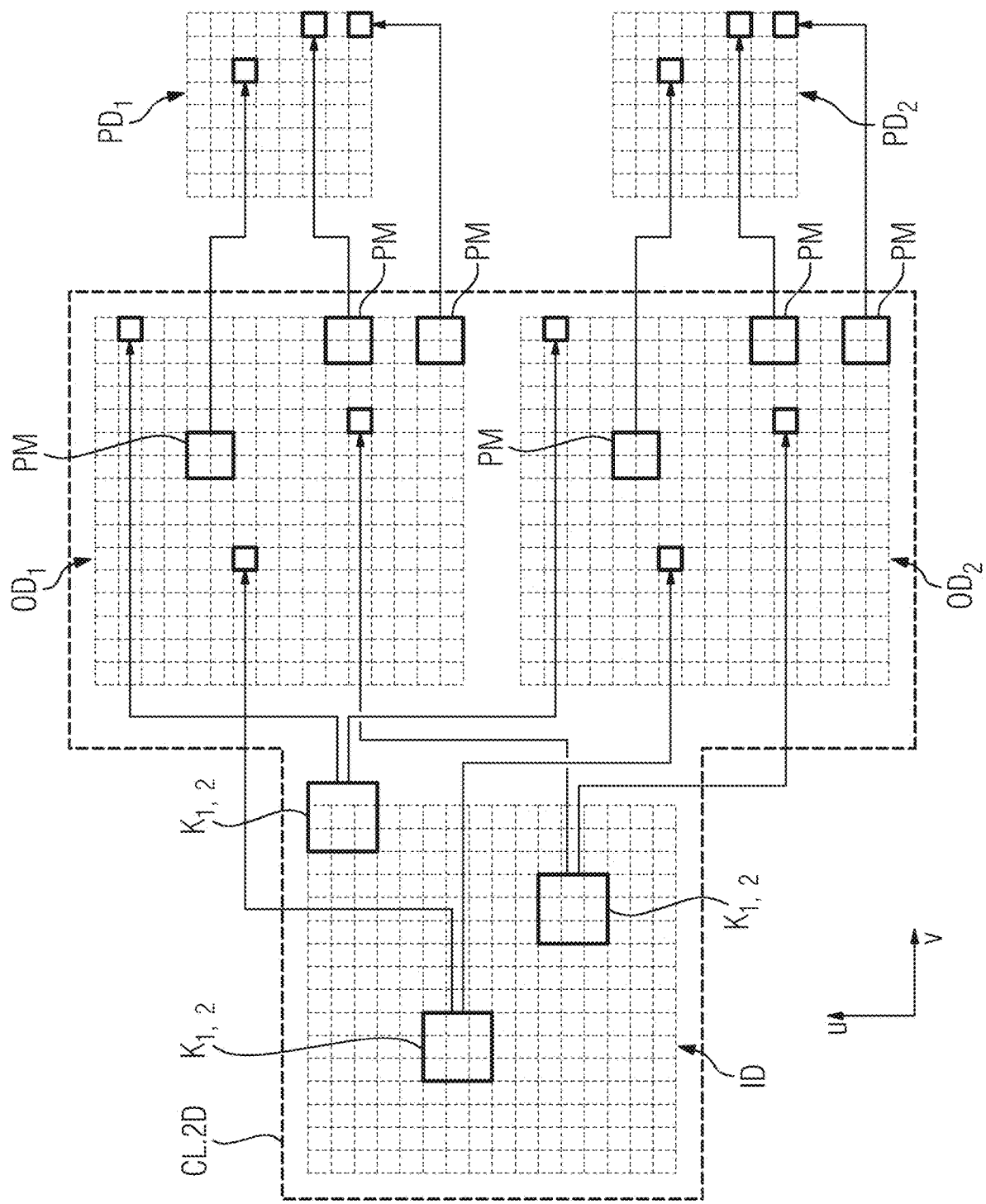
FIG. 7 shows a two-dimensional convolution layer and a pooling layer of a convolutional neuronal network.

FIG. 7 shows a two-dimensional convolution layer CL.2D and a pooling layer of a convolutional neuronal network, in particular of the second subnetwork G.2D. The two-dimensional convolution layer CL.2D shown realizes a two-dimensional convolutional operator.

The two-dimensional convolution layer maps a two-dimensional input array (which in this example embodiment is an input image, which has 8×8 pixels) to two two-dimensional output arrays, wherein the extent of the two-dimensional input array and each of the two-dimensional output arrays is identical in relation to each dimension. The first output array is a convolution of the input array with a first kernel $K_1$, the second output array is a convolution of the input array with a second kernel $K_2$:

$$(ID * K_{1,2})[n_1, n_2] = \sum_{n'_1=1}^{N_1} \sum_{n'_2=1}^{N_2} ID[n'_1, n'_2] \cdot K_{1,2}[n_1 - n'_1, n_2 - n'_2]$$

Here ID $[n_1, n_2]$ or $K_{1,2}[n_1, n_2]$ refers to the entry of the input array or of the kernel with the indices of coordinates $n_1$, $n_2$. or of the kernel $K_1$, $K_2$ to the indices (coordinates) $n_1$ and $n_2$. Here ID $[n_1, n_2]=0$ or $K_{1,2}[n_1, n_2]=0$, if one of the two indices lies outside of the valid range. As an alternative other boundary conditions or boundary values (for example periodic boundary conditions or boundary values) can be used. $N_1$ is the extent of the input image in the first direction u, $N_2$ is the extent of the input image in the second direction v, measured in each case in a number of pixels. The result is designated $DL_{1,2} := ID * K_{1,2}$.

A convolution can be defined in the same way in any given dimensions, i.e. map d-dimensional input images to d-dimensional output images, in particular in three dimensions:

$$(ID^* K_{1,2})[n_1, n_2, n_3] = \sum_{n'_1=1}^{N_1} \sum_{n'_2=1}^{N_2} \sum_{n'_3=1}^{N_3} ID[n'_1, n'_2, n'_3] \cdot K_{1,2}[n_1 - n'_1, n_2 - n'_2, n_3 - n'_3]$$

The kernel $K_1$, $K_2$ here is defined by a kernel mask and by kernel values. The kernel mask here is the extent of the kernel (the valid indices), and the kernel values are the actual values of the kernel. The kernel mask can be specified in particular by the size in pixels and/or voxels, the kernel values in the form of an array. For example $$K = \begin{pmatrix} -1 & 1 & -1 \\ 1 & 1 & 1 \\ -1 & 1 & -1 \end{pmatrix} = \begin{pmatrix} K[-1,-1] & K[-1,0] & K[-1,1] \\ K[0,-1] & K[0,0] & K[0,1] \\ K[1,-1] & K[1,0] & K[1,1] \end{pmatrix}$$

can be used as a kernel with the extent 3×3 pixels. It is also possible to used non-rectangular or non square-shaped kernel masks. However these can be handled in a similar way to rectangular or square-shaped kernel masks, if all kernel values outside of the kernel mask are occupied by 0.

In the example embodiment shown the convolutional operator is realized within an artificial neural network. The input array here corresponds to a first layer of the artificial neural network, and the one or more output arrays correspond to a second layer of the artificial neural network, wherein the first and the second layer are neighboring layers in the artificial neural network. The kernel mask is produced by the topology (structure of the edges and nodes) of the artificial neural network, the kernel values by the edge weights. Thus in this example embodiment only the kernel value are changed by the training of the artificial neural network, not the kernel mask. During training edge weights for the same entry are only changed simultaneously in the kernel mask in each case for this in order to achieve the kernel or the kernel values being the same for each entry of the output array.

The example embodiment shown, as well as the two-dimensional convolutional operator CL.2D, also comprises a two-dimensional pooling operator in the form of a pooling layer. This maps a two-dimensional input array $OD_{1,2}$ to a two-dimensional output array $PD_{1,2}$, wherein the extent of the two-dimensional output array $PD_{1,2}$ in relation to at least one first dimension is smaller than the extent of the two-dimensional input array $OD_{1,2}$ in relation to this first dimension. In the example embodiment shown a maximum value pooling of 2×2 pixels in each case is used, the output array $PD_{1,2}$ is thus produced from $$PD_{1,2}[n_1, n_2] = \max\left\{\begin{matrix} OD_{1,2}[2n_1, 2n_2], OD_{1,2}[2n_1, 2n_2+1], \\ OD_{1,2}[2n_1+1, 2n_2], OD_{1,2}[2n_1+1, 2n_2+1] \end{matrix}\right\}$$

The region to be pooled (here in each case a region of 2×2 pixels) is also referred to as the pooling mask.

The first subnetwork and/or the second subnetwork can also be an unpooling operator. This maps an input array to an output array, wherein the extent of the output array in relation to at least one dimension is larger than the extent of the input array. In the two-dimensional case for example the number of the pixels can be multiplied by four, in that 2×2 pixels of the output array are created from one pixel of the input array. For example each of the 2×2 pixels can receive the value of the one pixel of the input array, as an alternative just one pixel of the 2×2 pixels of the output array can receive the value of the one pixel of the input array and the other pixels can be occupied by the value 0.

Both a pooling operator and also an unpooling operator, as in the example embodiment shown, can be realized by an artificial neural network.

FIG. 8 shows the data structure during removal RMV of a two-dimensional layer w.1, w.2, w.7, w.8 of the three-dimensional mammography dataset x via the processing unit. In this example embodiment the removal RMV is carried out multiple times, and creates from the first three-dimensional mammography dataset x a second three-dimensional mammography dataset x', wherein the second three-dimensional mammography dataset x' comprises fewer voxels than the first three-dimensional mammography dataset x.

Both the first and also the second three-dimensional mammography dataset x, x' are extended in a first direction u, in a second direction v and a third direction w, wherein the second direction v is orthogonal to the first direction u, and wherein the third direction w is orthogonal to the first direction and to the second direction v.

The extent of the first and of the second three-dimensional mammography dataset x, x' in the first direction u is $L_1$ voxels, the extent of the first and of the second three-dimensional mammography dataset x, x' in the second direction v is $L_2$ voxels. The extent of the first three-dimensional mammography dataset x in the third direction w is $L_3$ voxels, the extent of the second three-dimensional mammography dataset x' in the third direction w is $L_3'$ voxels, wherein $L_3' < L_3$. In this example embodiment $L_1 = L_2 = L_3 = 8$, and $L_3' = 4$. In this example embodiment the method step removal RMV will therefore be carried out four times. Naturally it is also possible to use other extents of the first and of the second three-dimensional mammography dataset x, x'.

The first three-dimensional mammography dataset x in this example embodiment comprise eight two-dimensional layers w.1, . . . , w.8, the second three-dimensional mammography dataset x' in this example embodiment comprises four two-dimensional layers w.3, . . . , w.6. Each of these two-dimensional layers w.1, . . . , w.8 is extended in the first direction u and in the second direction v and comprises L1•L2 voxels or pixels. This in the four-times repetition of the method step removal RMV, the two-dimensional layers w.1, w.2, w.7 and w.8 are removed.

The layers w.1, w.2, w.7, w.8 to be removed are determined in this example embodiment based on the position of a nipple in the first three-dimensional mammography dataset x. In particular the two-dimensional nipple layer w.B is determined from the two-dimensional layers w.1, . . . , w.8 of the first three-dimensional mammography dataset x, which comprises the position of the nipple. The determination of the two-dimensional nipple layer w.B is undertaken here by a further convolutional neural network, which receives as its input data a three-dimensional mammography dataset x and creates as an output value the coordinates of the two-dimensional nipple layer w.B. This further convolutional neural network is trained by way of a plurality of training pairs, wherein each of the training pairs comprises a three-dimensional training mammography dataset x.1, . . . , x.S as well as an associated training position or training layer, wherein the training position or training layer corresponds to the position or the layer of the nipple in the three-dimensional training mammography dataset x.1, . . . , x.S and has been determined by a user.

As an alternative the layers w.1, w.2, w.7, w.8 to be removed can be determined based on weighting factors of voxels of the three-dimensional mammography dataset x. The weighting factors can in particular correspond to a probability value that the associated voxel is mapping a lesion. The weighting factors for the voxel of the three-dimensional mammography dataset x can be determined in particular by a further convolutional neural network, which receives as its input data a three-dimensional mammography dataset x and creates as its output value a three-dimensional weighting dataset, which allocates to each of the voxels of the three-dimensional mammography dataset x the probability value that voxel is mapping a lesion. The further convolutional neural network can be trained in particular based on training pairs, wherein each training pair comprises a three-dimensional training mammography dataset x.1, . . . , x.S as well as an associated training segmentation, wherein the training segmentation is undertaken by a user, which segments lesions in the three-dimensional training mammography datasets x.1, . . . , x.S. The layers w.1, w.2, w.7, w.8 to be removed are based in the example embodiment shown on the two-dimensional weighting layer w.G, wherein the two-dimensional weighting layer w.G is the two-dimensional layer w.1, . . . , w.8, which comprises the voxels, to which the maximum weighting factor is assigned.

In this example embodiment both the two-dimensional breast layer w.B and also the two-dimensional weighting layer w.G are identical to the two-dimensional layer w.4. In both alternatives the two-dimensional layers w.1, w.2, w.7, w.8 to be removed are determined such that the resulting second three-dimensional mammography dataset x' has a defined extent $L_3'$ in the third direction w, and that the two-dimensional breast layer w.B or the two-dimensional weighting layer w.G is the central layer (for odd $L_3'$) or one of the two central layers (for even $L_3'$).

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a two-dimensional mammography dataset, comprising:
   receiving a three-dimensional mammography dataset of an examination region via an interface; and
   determining a two-dimensional mammography dataset of the examination region by application of a trained generator function to the three-dimensional mammography dataset received via a processing unit, wherein the trained generator function is based on a trained GA algorithm.

2. The method of claim 1, wherein the trained GA algorithm includes a generative function and a classifying function, and wherein the trained generator function is identical to a generative subnetwork of the trained GA algorithm.

3. The method of claim 2, wherein the trained generator function is an artificial neural network.

4. The method of claim 2, wherein the trained generator function includes a concatenation of a first subfunction, a first projection function and a second subfunction, and wherein the determining of the two-dimensional mammography dataset of the examination region includes
   mapping, via the first subfunction, the three-dimensional mammography dataset to a first feature vector,
   mapping, via the first projection function, the first feature vector to a second feature vector, and
   mapping, via the second subfunction, the second feature vector to the two-dimensional mammography dataset.

5. The method of claim 2, wherein the two-dimensional mammography dataset is extended in relation to a first direction and is extended in relation to a second direction, the method further comprising:
   removing a two-dimensional layer of the three-dimensional mammography dataset via the processing unit, wherein the two-dimensional layer is extended in relation to the first direction and is extended to the second direction.

6. The method of claim 5, wherein the two-dimensional layer is determined based on a position of a nipple in the three-dimensional mammography dataset.

7. The method of claim 5, wherein the two-dimensional layer is determined based on weighting factors of voxels of the three-dimensional mammography dataset.

8. The method of claim 2, wherein the two-dimensional mammography dataset comprises one or more pixels, and wherein the method further comprises:
   determining, in a second determination, a second two-dimensional probability dataset via the processing unit, wherein the second two-dimensional probability dataset assigns, to each respective pixel of the one or more pixels of the two-dimensional mammography dataset, a respective probability that the respective pixel is mapping a lesion.

9. A non-transitory computer program product storing a computer program, directly loadable into a memory of a determination system, including program sections for carrying out the method of claim 2, when the program sections are executed by the determination system.

10. A non-transitory computer-readable storage medium, storing program sections readable and executable by a determination system, for carrying out the method of claim 2, when the program sections are executed by the determination system.

11. The method of claim 1, wherein the trained generator function is an artificial neural network.

12. The method of claim 1, wherein the trained generator function includes a concatenation of a first subfunction, a first projection function and a second subfunction, and wherein the determining of the two-dimensional mammography dataset of the examination region includes
mapping, via the first subfunction, the three-dimensional mammography dataset to a first feature vector,
mapping, via the first projection function, the first feature vector to a second feature vector, and
mapping, via the second subfunction, the second feature vector to the two-dimensional mammography dataset.

13. The method of claim 12, wherein the first subfunction includes at least one three-dimensional convolutional operator.

14. The method of claim 13, wherein the second subfunction includes at least one two-dimensional convolutional operator.

15. The method of claim 13, wherein the projection function is a three-dimensional convolutional operator, wherein the two-dimensional mammography dataset is extended in relation to a first direction and in relation to a second direction, wherein the three-dimensional mammography dataset is extended in relation to a third direction, and wherein an extent of a convolution kernel of the three-dimensional convolutional operator, in relation to the third direction, is based on an extent of the three-dimensional mammography dataset in relation to the third direction.

16. The method of claim 12, wherein the second subfunction includes at least one two-dimensional convolutional operator.

17. The method of claim 16, wherein the projection function is a three-dimensional convolutional operator, wherein the two-dimensional mammography dataset is extended in relation to a first direction and in relation to a second direction, wherein the three-dimensional mammography dataset is extended in relation to a third direction, and wherein an extent of a convolution kernel of the three-dimensional convolutional operator, in relation to the third direction, is based on an extent of the three-dimensional mammography dataset in relation to the third direction.

18. The method of claim 12, wherein the projection function is a three-dimensional convolutional operator, wherein the two-dimensional mammography dataset is extended in relation to a first direction and in relation to a second direction,
wherein the three-dimensional mammography dataset is extended in relation to a third direction, and wherein an extent of a convolution kernel of the three-dimensional convolutional operator, in relation to the third direction, is identical to an extent of the three-dimensional mammography dataset, corrected based on effects of at least one of a pooling operator and an unpooling operator of the first subfunction, in relation to the third direction.

19. The method of claim 1, wherein the two-dimensional mammography dataset is extended in relation to a first direction and is extended in relation to a second direction, the method further comprising:
removing a two-dimensional layer of the three-dimensional mammography dataset via the processing unit, wherein the two-dimensional layer is extended in relation to the first direction and is extended to the second direction.

20. The method of claim 19, wherein the two-dimensional layer is determined based on a position of a nipple in the three-dimensional mammography dataset.

21. The method of claim 19, wherein the two-dimensional layer is determined based on weighting factors of voxels of the three-dimensional mammography dataset and wherein a weighting factor of a respective voxel, of the voxels, corresponds to a probability that the respective voxel is mapping a lesion.

22. The method of claim 1, wherein the two-dimensional mammography dataset comprises one or more pixels, and wherein the method further comprises:
determining, in a second determination, a second two-dimensional probability dataset via the processing unit, wherein the second two-dimensional probability dataset assigns, to each respective pixel of the one or more pixels of the two-dimensional mammography dataset, a respective probability that the respective pixel is mapping a lesion.

23. A non-transitory computer program product storing a computer program, directly loadable into a memory of a determination system, including program sections for carrying out the method of claim 1, when the program sections are executed by the determination system.

24. A non-transitory computer-readable storage medium, storing program sections readable and executable by a determination system, for carrying out the method of claim 1, when the program sections are executed by the determination system.

25. A determination system, comprising:
an interface, embodied to receive a three-dimensional mammography dataset of an examination region;
at least one processor, embodied to determine a two-dimensional mammography dataset of the examination region by application of a trained generator function to the three-dimensional mammography dataset received, wherein the trained generator function is based on a trained GA algorithm.

26. A determination system of claim 25, wherein the trained GA algorithm includes a generative function and a classifying function, and wherein the trained generator function is identical to a generative subnetwork of the trained GA algorithm.

27. A mammography unit, comprising the determination system of claim 25.

* * * * *